(12) United States Patent
Slone

(10) Patent No.: US 8,007,539 B2
(45) Date of Patent: Aug. 30, 2011

(54) METAL-ON-METAL MODULAR HYBRID LINER

(75) Inventor: W. Jason Slone, Silver Lake, IN (US)

(73) Assignee: Biomet Manufacturing Corp., Warsaw, IN (US)

(*) Notice: Subject to any disclaimer, the term of this patent is extended or adjusted under 35 U.S.C. 154(b) by 302 days.

(21) Appl. No.: 12/329,651

(22) Filed: Dec. 8, 2008

(65) Prior Publication Data

US 2010/0145466 A1 Jun. 10, 2010

(51) Int. Cl.
*A61F 2/32* (2006.01)

(52) U.S. Cl. ............... 623/22.15; 623/22.14; 623/22.17; 623/22.19; 623/22.2

(58) Field of Classification Search .... 623/22.11–22.39; A61F 2/32
See application file for complete search history.

(56) References Cited

U.S. PATENT DOCUMENTS

| | | | |
|---|---|---|---|
| 2,668,531 A | 2/1954 | Haboush | |
| 3,067,740 A | 12/1962 | Haboush | |
| 3,584,318 A | 6/1971 | Scales et al. | |
| 3,740,769 A | 6/1973 | Haboush | |
| 3,815,157 A | 6/1974 | Skorecki et al. | |
| 3,875,593 A | 4/1975 | Shersher | |
| 4,619,658 A | 10/1986 | Pappas et al. | |
| 4,642,123 A | 2/1987 | Noiles | |
| 4,676,798 A | 6/1987 | Noiles | |
| 4,908,033 A * | 3/1990 | Frey et al. .................. | 623/22.19 |
| 4,978,356 A | 12/1990 | Noiles | |
| 5,019,105 A | 5/1991 | Wiley | |
| 5,108,447 A * | 4/1992 | Zeiler et al. ................ | 623/22.14 |
| 5,133,763 A | 7/1992 | Mullers et al. | |
| 5,314,491 A | 5/1994 | Thongpreda et al. | |
| 5,413,603 A | 5/1995 | Noiles et al. | |
| 5,425,779 A | 6/1995 | Schlosser et al. | |
| 5,755,807 A | 5/1998 | Anstaett et al. | |
| 5,800,555 A | 9/1998 | Gray, III | |
| 5,824,108 A | 10/1998 | Huebner | |
| 5,879,404 A * | 3/1999 | Bateman et al. ........... | 623/22.21 |
| 5,989,293 A | 11/1999 | Cook et al. | |
| 6,042,611 A | 3/2000 | Noiles | |
| 6,093,208 A | 7/2000 | Tian et al. | |
| 6,475,243 B1 | 11/2002 | Sheldon et al. | |
| 6,682,566 B2 | 1/2004 | Draenert et al. | |
| 6,916,342 B2 | 7/2005 | Frederick et al. | |
| 2002/0068980 A1* | 6/2002 | Serbousek et al. ......... | 623/22.29 |
| 2003/0125810 A1 | 7/2003 | Sullivan et al. | |

(Continued)

FOREIGN PATENT DOCUMENTS

DE 19813074 A1 9/1999

(Continued)

OTHER PUBLICATIONS

European Search Report mailed Apr. 23, 2010 for European Application EP09178414 which claim benefit of U.S. Appl. No. 12/329,651, filed Dec. 8, 2008.

(Continued)

*Primary Examiner* — David Isabella
*Assistant Examiner* — Jason-Dennis Stewart
(74) *Attorney, Agent, or Firm* — Harness, Dickey

(57) ABSTRACT

A prosthetic joint assembly that includes a shell including an inner surface. The assembly also includes a bearing member including an outer surface. The bearing member is received by the shell such that the outer surface of the bearing member is adjacent the inner surface of the shell. Furthermore, the joint assembly includes a compressible member that is rigidly fixed to the inner surface of the shell or the outer surface of the bearing member to only cover a portion thereof. The compressible member is made of a material that is different from the shell or the bearing member.

21 Claims, 3 Drawing Sheets

U.S. PATENT DOCUMENTS

2004/0225369 A1 11/2004 Lakin et al.
2005/0146070 A1 7/2005 Muratoglu et al.

FOREIGN PATENT DOCUMENTS

| EP | 0298234 A1 | 1/1989 |
| EP | 0445068 A1 | 9/1991 |
| WO | WO-0124739 A2 | 4/2001 |
| WO | WO-2008130989 A2 | 10/2008 |

OTHER PUBLICATIONS

"A Technical Report," brochure, RingLoc Acetabular Series, (Sep. 1995) Biomet, Inc., 4 pages.
"Uniting versitile design with unparalleled locking technology," brochure, RingLoc Acetabular Series, (Dec. 2006) Biomet, Inc., 6 pages.

* cited by examiner

METAL-ON-METAL MODULAR HYBRID LINER

FIELD

This invention relates to a prosthetic joint and, more particularly, to a metal-on-metal modular hybrid liner for a prosthetic joint.

BACKGROUND

The statements in this section merely provide background information related to the present disclosure and may not constitute prior art.

Prosthetic joints can reduce pain due to arthritis, deterioration, deformation, and the like. For instance, hip joint prosthetic assemblies often include femoral components (i.e., components attached to a resected femur) and pelvic components (i.e., components attached to a pelvis), and the femoral components are movably coupled to the pelvic components to replicate the mechanics of the anatomical hip joint. More specifically, pelvic components of a hip joint prosthetic assembly can include a shell and a liner. The shell fixes to the patient's pelvis, within the acetabulum, and the shell receives the liner. The liner fixes to the shell and is coupled to a head of the femoral component of the prosthesis. Accordingly, the liner receives the head of the femoral component, and the head articulates on an inner surface of the liner.

Oftentimes, the shell and liner are secured against relative rotational movement by a taper lock. Furthermore, in some assemblies, the shell and liner are retained using a ring lock feature. Specifically, a ring member affixes to one or both of the shell and the liner and interferes with movement of the liner axially away from and out of the shell. Additionally, some prosthesis assemblies include a polymeric inner member disposed between the shell and the liner. The inner member covers the outer surface of the liner and can resiliently flex when being inserted into the shell to provide an adequate fit.

SUMMARY

A prosthetic joint assembly is disclosed. The assembly includes a shell including an inner surface. The assembly also includes a bearing member including an outer surface. The bearing member is received by the shell such that the outer surface of the bearing member is adjacent the inner surface of the shell. Furthermore, the joint assembly includes a compressible member that is rigidly fixed to the inner surface of the shell or the outer surface of the bearing member to only cover a portion thereof. The compressible member is made of a material that is different from the shell or the bearing member.

In another aspect, a liner assembly of a prosthetic joint assembly is disclosed. The joint assembly includes a ring member and a shell that includes an inner surface with a groove that receives the ring member. The liner assembly includes a bearing member that includes an outer surface. The bearing member is received by the shell such that the outer surface of the bearing member is adjacent the inner surface of the shell. Furthermore, the liner assembly includes a compressible member that is rigidly fixed to the outer surface of the bearing member. The compressible member is made of a material that is different than that of the bearing member. The compressible member includes a groove that receives the ring member to limit relative movement between the bearing member and the shell.

In still another aspect, a prosthetic joint assembly is disclosed. The assembly includes a shell made out of a metallic material or a ceramic material. The joint assembly also includes a bearing member that is made out of a metallic material or a ceramic material. The bearing member is received by the shell. Furthermore, the joint assembly includes an anti-rotation device that includes a protrusion and a recessed surface. The protrusion is fixed to the shell or the bearing member, and the recessed surface is included in the other of the shell and the bearing member. The recessed surface receives the protrusion to limit relative rotation between the shell and the bearing member.

Still further, a method of implanting a prosthesis assembly is disclosed in another aspect. The method includes selecting a shell that includes a groove. The method also includes selecting a liner assembly that includes a bearing member and a compressible member. The compressible member is rigidly fixed to an outer surface of the bearing member. The compressible member only partially covers the outer surface and includes a groove. The compressible member is made out of a material that is different from the bearing member. Furthermore, the method includes securing the liner assembly within the shell with a ring member such that the ring member is disposed within the groove of the shell and the groove of the compressible member.

Moreover, a prosthetic joint assembly is disclosed in still another aspect. The joint assembly includes a metallic shell including an inner surface, a groove, and a rim. The joint assembly also includes a metallic bearing member including an outer surface, a rim, and an apex. The bearing member is received by the shell such that the outer surface of the bearing member is adjacent the inner surface of the shell. Furthermore, the joint assembly includes an anti-rotation device that includes a projection that projects from the rim of the shell and a recessed surface included on the rim of the bearing member. The projection is received by the recessed surface to limit relative rotation between the bearing member and the shell. Furthermore, the joint assembly includes a first annular polymeric compressible member that is rigidly fixed to the outer surface of the bearing member on the rim. The first compressible member includes a groove, and the first compressible member is disposed between the recessed surface and the projection. The first compressible member also has a modulus of elasticity lower than that of the shell and the bearing member. Furthermore, the joint assembly includes a second annular polymeric compressible member that is rigidly fixed to the outer surface of the bearing member between the rim and the apex. The second compressible member also has a modulus of elasticity lower than that of the shell and the bearing member. In addition, the joint assembly includes a ring member that is disposed within the groove of the shell and the groove of the first compressible member. The ring member limits actual movement of the bearing member away from the shell.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

DETAILED DESCRIPTION

Figure 1:
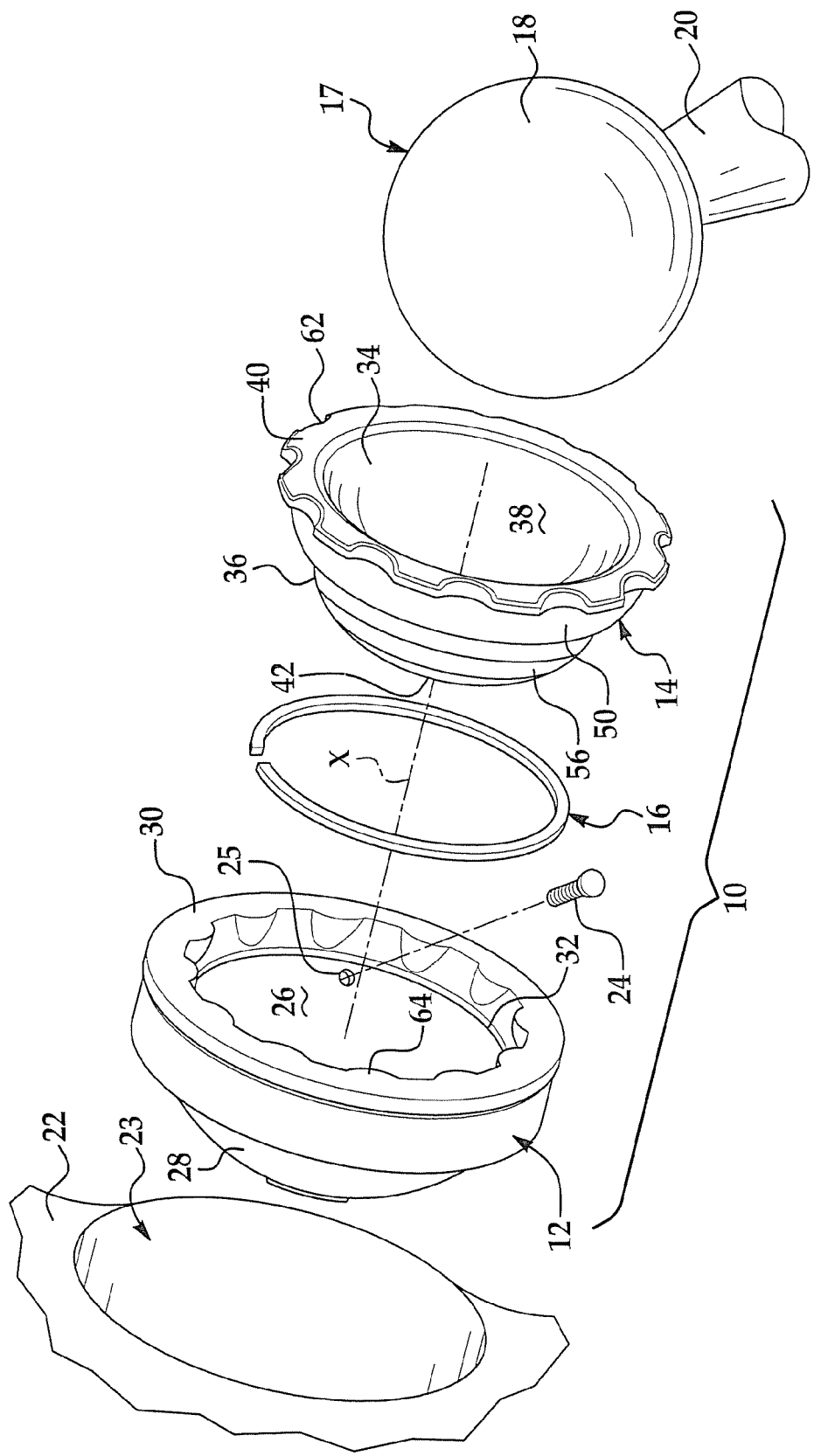
FIG. 1 is an exploded view of a prosthetic joint assembly according to various embodiments of the present disclosure.

The following description is merely exemplary in nature and is not intended to limit the present disclosure, application, or uses. It should be understood that throughout the drawings, corresponding reference numerals indicate like or corresponding parts and features.

Figure 2:
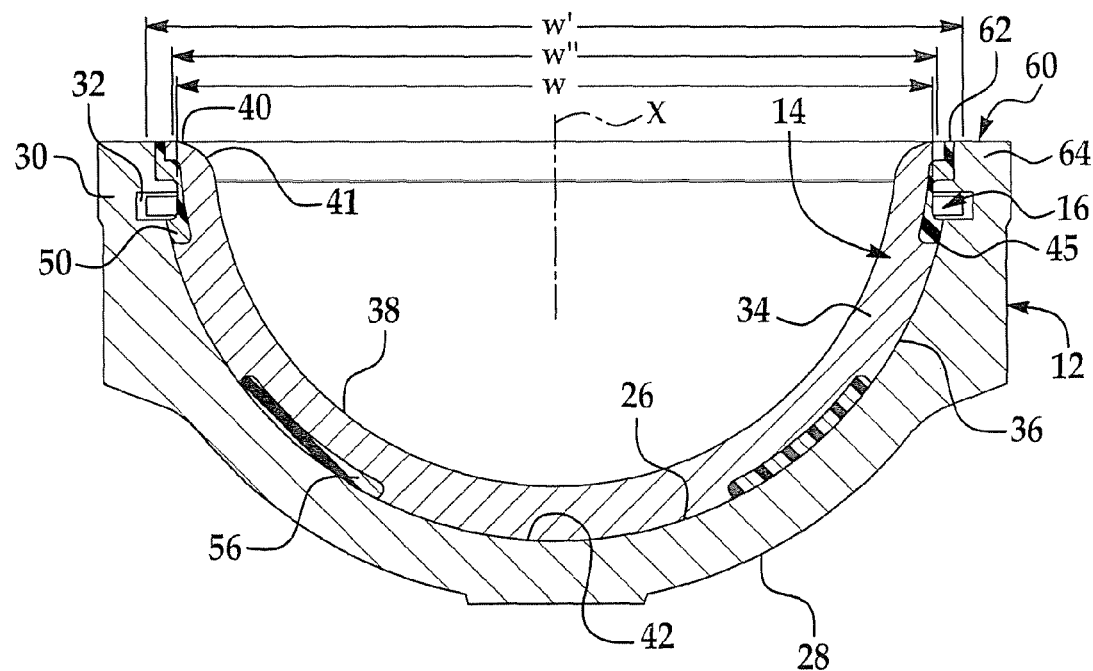
FIG. 2 is a sectional view of the prosthetic joint assembly of FIG. 1.

Referring initially to FIGS. 1 and 2, a prosthetic joint assembly 10 is illustrated. The joint assembly 10 generally includes a shell 12, a liner assembly 14, and a ring member 16. In the embodiment shown, for instance, the joint assembly 10 is a hip joint prosthetic assembly 10; however, the joint assembly 10 could be useful for any suitable joint other than the hip joint. The joint assembly 10 can be operably coupled to a femoral component 17 having a head 18, a neck 20, and a stem (not shown). The femoral component 17 can be fixed to a resected femur (not shown), and the head 18 can be received by the liner assembly 14. More specifically, the head 18 can be movably coupled to the liner assembly 14 for pivotal movement therein.

Furthermore, the shell 12 can be received in and fixedly coupled to a pelvis 22 within an acetabulum 23 thereof. In some embodiments, the shell 12 is fixed to the pelvis 22 via one or more fasteners 24. More specifically, the shell 12 includes one or more apertures 25 (FIG. 1), and the fasteners 24 extend through corresponding apertures 25 to attach the shell 12 to the pelvis 22. In other embodiments, bone cement, adhesive, etc. (not shown) is used to fix the shell 12 to the pelvis 22. Moreover, in some embodiments, both fasteners 24 and bone cement, adhesive, etc. (not shown) is used for this purpose. However, it will be appreciated that the shell 12 can be fixed to the pelvis 22 in any suitable manner. In addition, the shell 12 receives the liner assembly 14 in a manner to be discussed in greater detail below.

The shell 12 can have a dome-like shape so as to include an inner surface 26 (i.e., bearing-engaging surface) and an outer surface 28 (i.e., bone engaging surface). The outer surface 28 can be relatively porous to facilitate fixation of the shell 12 to the pelvis 22. Also, the apertures 25 can be countersunk on the inner surface 26 to allow the fasteners 24 to be disposed beneath the inner surface 26 when used to attach the shell 12 to the pelvis 22. Moreover, the shell 12 includes an axis X. Furthermore, the shell 12 includes a rim 30 and a groove 32. In some embodiments, the groove 32 is annular and extends inwardly from the inner surface 26, transverse to the axis X, and adjacent the rim 30.

The shell 12 can be made out of any suitable material. For instance, in some embodiments, the shell 12 is made out of metal, such as cobalt, chrome, titanium, titanium alloy, etc. Also, in some embodiments, the shell 12 is made out of a ceramic material. The shell 12 can be made using any suitable manufacturing process. For instance, in some embodiments, the shell 12 is cast or wrought.

Furthermore, in some embodiments, the ring member 16 is substantially flat and annular. In some embodiments represented in FIG. 1, the ring member 16 is notched so as to be discontinuous. As shown in FIG. 2, the ring member 16 defines an inner width W and an outer width W'. Because the ring member 16 is notched, the ring member 16 can flex so as to change the inner width W and an outer width W'.

Now referring generally to FIGS. 1-5, the liner assembly 14 will be discussed in greater detail. The liner assembly 14 includes a bearing member 34. The bearing member 34 can have a dome-like shape so as to include an outer surface 36 (i.e., shell-engaging surface), an inner surface 38 (i.e., articulating surface), and a rim 40. Furthermore, the bearing member 34 can include a radius 41 formed on the inner surface 38 adjacent the rim 40. In some embodiments, the radius can measure between approximately 0.050 and approximately 0.250 inches. Additionally, the bearing member 34 can include an apex 42. In some embodiments, the bearing member 34 substantially shares the axis X with the shell 12.

Figure 5:
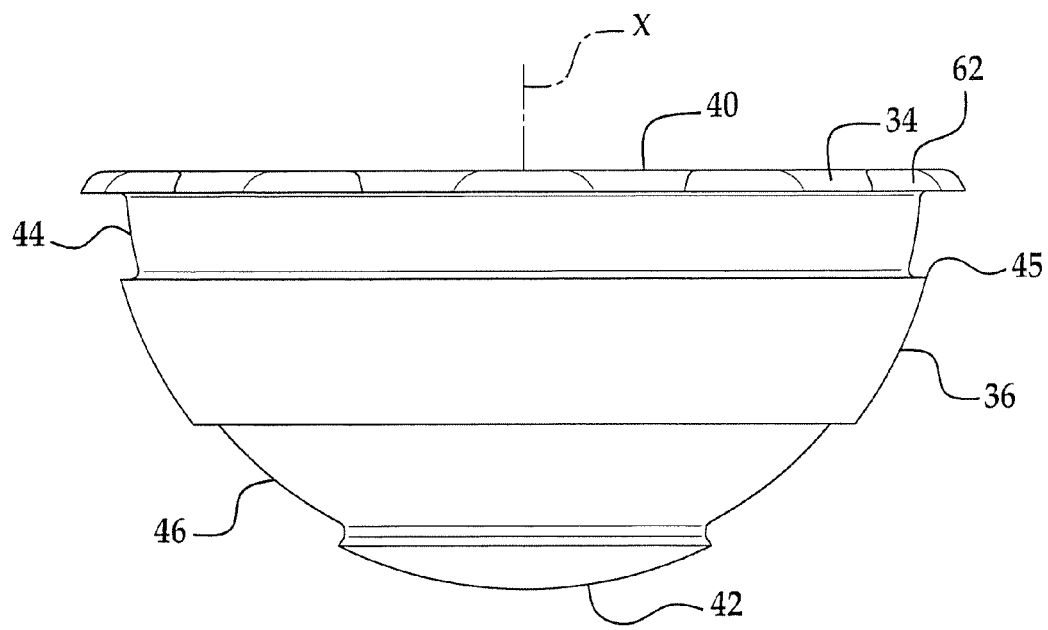
FIG. 5 is a side view of a bearing member of the liner assembly of FIG. 3.

Moreover, in some embodiments, the bearing member 34 can include a first recess 44 and a second recess 46 (FIG. 5). In the embodiments represented in FIG. 5, the first and second recesses 44, 46 are both annular. The first recess 44 can be disposed adjacent the rim 40 of the bearing member 34. The second recess 46 can be disposed between the rim 40 and the apex 42 of the bearing member 34. Furthermore, the first recess 44 can include a lower lip 45. The lower lip 45 has a width W" as shown in FIG. 2.

Figure 4:
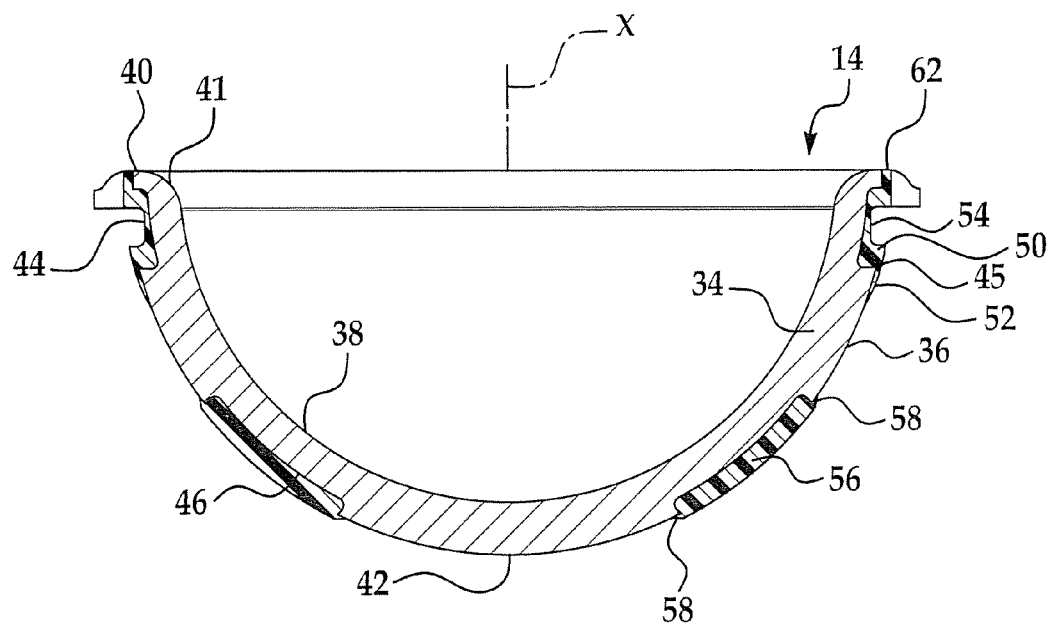
FIG. 4 is a sectional view of the liner assembly of FIG. 3.

Furthermore, as shown in FIGS. 2 and 4, the liner assembly 14 can include a first compressible member 50. The first compressible member 50 can be substantially annular and can be disposed in the first recess 44 and can extend about the rim 40 of the bearing member 34. Furthermore, the first compressible member 50 can include an outer portion 52 (FIG. 4), which extends out from the first recess 44. It will be appreciated that the first compressible member 50 covers only a portion of the outer surface 36 of the bearing member 34. Furthermore, in some embodiments, the first compressible member 50 is rigidly fixed to the bearing member 34.

The first compressible member 50 can also include a groove 54. In some embodiments, the groove 54 is annular and is disposed in and extends about the first recess 44 as illustrated in FIG. 4. As will be discussed, the groove 54 receives the ring member 16 to thereby operatively secure the liner assembly 14 to the shell 12.

Additionally, the liner assembly 14 can include a second compressible member 56. In some embodiments, the second compressible member 56 is annular in shape and is disposed in the second recess 46. Moreover, as shown in FIG. 4, the second compressible member 56 can include an outer portion 58, which extends out from the second recess 46. It will be appreciated that the second compressible member 56 covers only a portion of the outer surface 36 of the bearing member 34. Moreover, in some embodiments, the second compressible member 56 is rigidly fixed to the bearing member 34.

The first and second compressible members 50, 56 can be made out of any suitable material. For instance, in some embodiments, the first and/or second compressible members 50, 56 are made out of a polymeric material, such as polyethylene or PEEK. Accordingly, in some embodiments, the first and second compressible members 50, 56 are made of a material that is different from the bearing member 34 and the shell 12. Furthermore, in some embodiments, the first and second compressible members 50, 56 have a modulus of elasticity that is lower than that of the bearing member 34 and the shell 12. As such, the compressible members 50, 56 can deflect and/or deform for achieving a stronger fit between the shell 12 and the liner assembly 14 as will be discussed.

Additionally, the first and second compressible members 50, 56 can be coupled to the bearing member 34 in using any suitable manufacturing process. For instance, in some embodiments, the first and second compressible members 50, 56 are injection molded or direct compression molded to the bearing member 34. The recesses 44, 46 can be dove-tailed or otherwise undercut in order to enhance engagement between the compressible members 50, 56 and the bearing member 34. Also, the outer surface 36 can have a roughened, textured surface within the recesses 44, 46 to facilitate engagement with the compressible members 50, 56. Additionally, the compressible members 50, 56 can be fixed to the bearing member 34 via an adhesive. Moreover, it will be appreciated that the first and second compressible members 50, 56 could be fixed to the shell 12 instead of the bearing member 34.

Accordingly, referring to FIGS. 1 and 2, the assembly of the prosthetic joint assembly 10 will be discussed in greater detail. Initially, the shell 12, the liner assembly 14, the ring member 16, and the femoral component 17 are each individually chosen according to anatomical dimensions of the patient and/or according to other factors. Then, the shell 12 is fixed to the pelvis 22. As mentioned above, the shell 12 can be fixed to the pelvis 22 within the acetabulum 23 via fasteners 24 and/or bone cement, adhesive, etc. Then, the ring member 16 is advanced axially into the groove 32 of the shell 12.

Subsequently, the liner assembly 14 is advanced along the axis X into the shell 12 so that the shell 12 receives the liner assembly 14 and the inner surface 26 of the shell 12 is adjacent the outer surface 36 of the liner assembly 14. It will be appreciated that the ring member 16 can resiliently flex to a wider width W until the liner assembly 14 advances enough to allow the ring member 16 to move into the groove 54 of the first compressible member 50. Once the ring member 16 is disposed in the groove 54 of the first compressible member 50 and the groove 32 of the shell 12, the ring member 16 operatively secures the liner assembly 14 and the shell 12 together such that the liner assembly 14 is limited from movement along the axis X away from the shell 12. Furthermore, when the ring member 16 is disposed in the grooves 54, 32, the ring member 16 can abut against both the liner assembly 14 and the shell 12 to substantially eliminate relative movement between the shell 12 and the liner assembly 14 for a secure fit.

Furthermore, it will be appreciated that the lower lip 45 of the bearing member 34 has a width W" that is larger than the inner width W of the ring member 16. Accordingly, the bearing member 34 can reinforce the first compressible member 50 for maintaining the tight fit between the shell 12 and the liner assembly 14.

In addition, it will be appreciated that the first and second compressible members 50, 56 can compress, deform and/or deflect due to abutment against the inner surface 26 of the shell 12. As such, the first and second compressible members 50, 56 can bias against the shell 12 and substantially eliminate any existing gaps between the inner surface 26 of the shell 12 and the outer surface 36 of the bearing member 34 to substantially eliminate micro-motion therebetween. As such, the first and second compressible member 50, 56 can make the fit tighter between the shell 12 and the liner assembly 14, and can help to more effectively distribute loads between the shell 12 and the liner assembly 14. Also, if, for instance, the shell 12 was deformed while being fixed to the pelvis 22, the first and second compressible members 50, 56 can substantially fill any resultant gaps between the liner assembly 14 and the shell 12.

Next, the femoral component 17, having already been attached to the femur (not shown), is coupled to the liner assembly 14. More specifically, the head 18 of the femoral component 17 is movably coupled to the liner assembly 14. As such, the head 18 articulates against the inner surface 38 of the liner assembly 14. It will be appreciated that the radius 41 of the bearing member 34 can effectively distribute any loads or stresses due to impingement between the neck 20 of the femoral component 17 and the liner assembly 14. As such, the liner assembly 14 is more likely to remain coupled to the shell 12, and the femoral component 17 is less likely to be notched due to impingement against the liner assembly 14.

Figure 3:
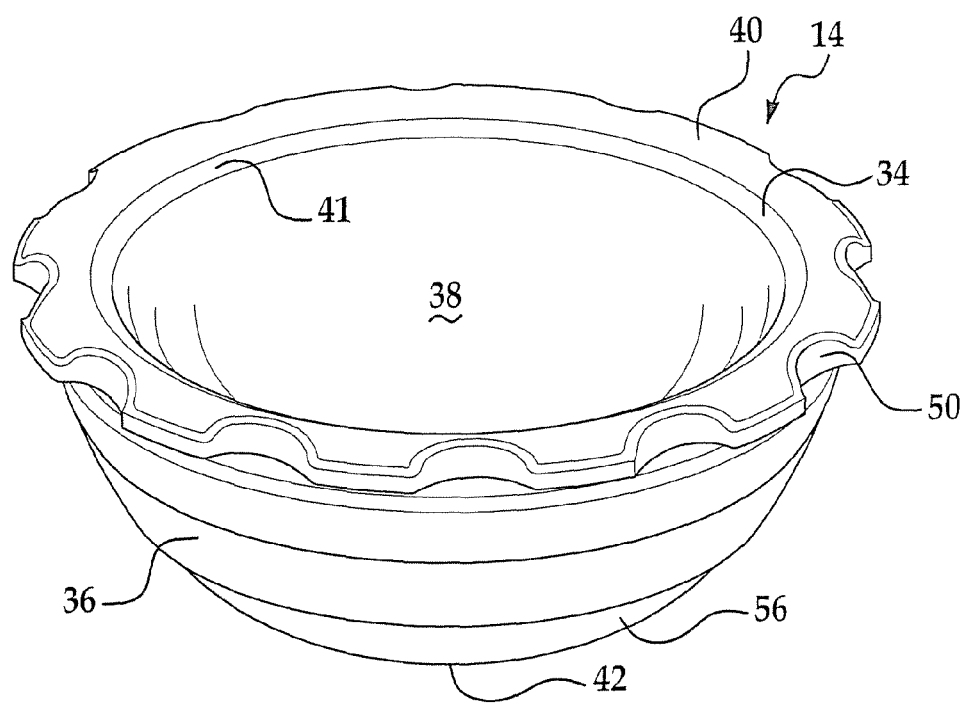
FIG. 3 is a perspective view of a liner assembly of the prosthetic joint assembly of FIG. 1.

As shown in FIGS. 1, 2, and 3, the joint assembly 10 also includes an anti-rotation device 60. Generally speaking, the anti-rotation device 60 includes a plurality of recessed surfaces 62 and a plurality of projections 64. In the embodiment shown, the recessed surfaces 62 are included on the rim 40 of the bearing member 34, and the projections 64 are fixed to the rim 40 of the shell 12. However, it will be appreciated that the recessed surfaces 62 could be included on the shell 12 and the projections 64 could be included on the bearing member 34.

In the embodiments illustrated in FIGS. 1, 2, and 3, the recessed surfaces 62 extend inwardly and transversely from the axis X on the liner assembly 14, and the plurality of recessed surfaces 62 are spaced evenly about the rim 40 of the bearing member 34. Also, the projections 64 are fixed to and extend toward the axis X from the rim 40 of the shell 12, and the projections 64 are evenly spaced about the rim 40 of the shell 12. Furthermore, the first compressible member 50 is coupled to the bearing member 34 so as to substantially cover each of the recessed surfaces 62.

During assembly, the liner assembly 14 presses into the shell 12, and the recessed surfaces 62 receive corresponding projections 64. It will be appreciated that the first compressible member 50 is disposed between the projections 64 and the recessed surfaces 62. The first compressible member 50 compresses and deflects enough to allow for a press fit between the projections 64 and the recessed surfaces 62. As such, the first compressible member 50 biases against the shell 12 to substantially eliminate micro-motion therebetween. Also, abutment between the projections 64 and the recessed surfaces 62 substantially limit rotation about the axis X, and the first compressible member 50 provides a substantially tight fit between the shell 12 and the liner assembly 14. Also, it will be appreciated that the recessed surfaces 62 substantially reinforce the first compressible member 50 so as to better distribute loads between the liner assembly 14 and the shell 12.

In summary, the prosthetic joint assembly 10 provides a high-strength coupling between the shell 12 and the liner assembly 14. The shell 12 can be tightly secured to the liner assembly 14, for instance, even if the shell 12 is deformed when being coupled to the pelvis 22. Furthermore, the first and second compressible members 50, 56 can deflect and/or deform in order to maintain the tight fit between the shell 12 and the liner assembly 14. Also, the shell 12 and liner assembly 14 can be rigidly secured with the ring member 16 and the anti-rotation device 60 for ease of installation. Moreover, it will be appreciated that the bearing member 34 can have a greater thickness than comparable devices of the current art because the recesses 44, 46 are localized, and because of this thickness, the bearing member 34 can be easier to manufacture within predetermined tolerances.

Moreover, the foregoing discussion discloses and describes merely exemplary embodiments of the present disclosure. One skilled in the art will readily recognize from such discussion, and from the accompanying drawings and claims, that various changes, modifications and variations may be made therein without departing from the spirit and scope of the disclosure as defined in the following claims. For instance, the sequence of the blocks of the method described herein can be changed without departing from the scope of the present disclosure.

What is claimed is:

1. A prosthetic joint assembly comprising:
   a shell including an inner surface and a groove;
   a bearing member including an outer surface, the bearing member being received by the shell such that the outer surface of the bearing member is adjacent the inner surface of the shell;
   a compressible member that is rigidly fixed to the outer surface of the bearing member to only cover a portion thereof, the compressible member including a groove, the compressible member being made of a material that is different from the bearing member; and
   a ring member that is received in the groove of the shell and the groove of the compressible member to limit relative movement of the shell and bearing member.

2. The prosthetic joint assembly of claim 1, wherein the bearing member includes a recess, and wherein the compressible member is disposed within the recess.

3. The prosthetic joint assembly of claim 2, wherein the compressible member extends out of the recess.

4. The prosthetic joint assembly of claim 1, wherein the bearing member includes a rim, and wherein the compressible member is annular and extends about the rim.

5. The prosthetic joint assembly of claim 1, wherein the bearing member includes a rim and an inner radius on the rim.

6. The prosthetic joint assembly of claim 1, wherein the bearing member includes at least one of a projection and a recessed surface that limits relative rotation between the shell and the bearing member, wherein the compressible member covers the at least one of the projection and the recessed surface so as to be disposed between the shell and the at least one of the projection and the recessed surface.

7. The prosthetic joint assembly of claim 1, wherein the bearing member includes an apex and a rim, wherein the compressible member is rigidly fixed to the bearing member between the apex and the rim, wherein the bearing member extends along an axis that extends through the apex and that extends inside the rim, and wherein the ring member limits relative movement of the shell and bearing along the axis.

8. The prosthetic joint assembly of claim 1, wherein a modulus of elasticity of the compressible member is lower than a modulus of elasticity of the bearing member.

9. The prosthetic joint assembly of claim 1, wherein the shell is made of metal, the bearing member is made of a metal, and the compressible member is made of a polymer.

10. The prosthetic joint assembly of claim 1, wherein the bearing member defines a first annular recess and a second annular recess, the first and second annular recesses disposed in spaced relationship to each other, and further comprising a first compressible member and a second compressible member, the first compressible member being disposed in the first annular recess, the first compressible member defining an annular groove, and the second compressible member being disposed in the second annular recess.

11. The prosthetic joint assembly of claim 1, wherein the ring member is separate from the compressible member, the bearing member, and the shell.

12. A liner assembly of a prosthetic joint assembly having a ring member and a shell that includes an inner surface with a groove that receives the ring member, the liner assembly comprising:
    a bearing member that includes an outer surface, the bearing member being received by the shell such that the outer surface of the bearing member is adjacent the inner surface of the shell; and
    a compressible member that is rigidly fixed to the outer surface of the bearing member, the compressible member being made of a material that is different than that of the bearing member, the compressible member including a groove that receives the ring member to limit relative movement between the bearing member and the shell.

13. The liner assembly of claim 12, wherein the bearing member is made of a metal and the compressible member is made of a polymer.

14. The liner assembly of claim 12, wherein the bearing member includes a recess, and wherein the compressible member is disposed within the recess such that the groove of the compressible member extends about the recess.

15. The liner assembly of claim 14, wherein the recess includes a lower lip having a width that is greater than an inner width of the ring member.

16. A prosthetic joint assembly comprising:
    a shell made of at least one of a metallic material and a ceramic material;
    a bearing member that is made of at least one of a metallic material and a ceramic material, the bearing member being received by the shell; and
    an anti-rotation device that includes a protrusion and a recessed surface, the protrusion fixed to one of the shell and the bearing member, the recessed surface included in the other of the shell and the bearing member, the recessed surface receiving the protrusion to limit relative rotation between the shell and the bearing member; and
    a compressible member that is made of a polymeric material and that is rigidly fixed to at least one of the shell and the bearing member so as to be disposed between the protrusion and the recessed surface.

17. The prosthetic joint assembly of claim 16, wherein the compressible member has a modulus of elasticity that is lower than a modulus of elasticity of the bearing member and a modulus of elasticity of the shell.

18. The prosthetic implant of claim 16, wherein the compressible member covers only a portion of an outer surface of the bearing member.

19. A prosthetic joint assembly comprising:
    a metallic shell including an inner surface, a groove, and a rim;
    a metallic bearing member including an outer surface, a rim, and an apex, the bearing member being received by the shell such that the outer surface of the bearing member is adjacent the inner surface of the shell;
    an anti-rotation device that includes a projection that projects from the rim of the shell and a recessed surface included on the rim of the bearing member, the projection received by the recessed surface to limit relative rotation between the bearing member and the shell;
    a first annular polymeric compressible member that is rigidly fixed to the outer surface of the bearing member on the rim, the first compressible member including a groove, the first compressible member disposed between the recessed surface and the projection, the first compressible member also having a modulus of elasticity lower than that of the shell and the bearing member;
    a second annular polymeric compressible member that is rigidly fixed to the outer surface of the bearing member between the rim and the apex, the second compressible member also having a modulus of elasticity lower than that of the shell and the bearing member; and
    a ring member that is disposed within the groove of the shell and the groove of the first compressible member, the ring member limiting axial movement of the bearing member away from the shell.

20. A prosthetic joint assembly comprising:
- a shell including an inner surface and a groove, the shell made of at least one of a metallic material and a ceramic material;
- a bearing member including an outer surface, the outer surface including a recess, the bearing member being received by the shell such that the outer surface of the bearing member is adjacent the inner surface of the shell, the bearing member made of at least one of a metallic material and a ceramic material;
- a first compressible member that is disposed at least partially within the recess of the bearing member and that is fixed to the outer surface of the bearing member to only cover a portion thereof, the first compressible member being made of a polymeric material, the first compressible member including a groove; and
- a ring member that is received in the groove of the shell and the groove of the first compressible member to limit relative movement of the shell and bearing member.

21. The prosthetic joint assembly of claim 20, further comprising a second compressible member that is made of a polymeric material, the second compressible member being rigidly fixed to the outer surface of the bearing member between a rim of the bearing member and an apex of the bearing member.

* * * * *